(12) United States Patent
Chan et al.

(10) Patent No.: US 11,568,727 B2
(45) Date of Patent: Jan. 31, 2023

(54) WEARABLE DEVICE AND METHOD OF OPERATING THE SAME

(71) Applicant: Wistron Corporation, New Taipei (TW)

(72) Inventors: Hsiang-Min Chan, New Taipei (TW); Yao-Tsung Chang, New Taipei (TW); Yin-Yu Chen, New Taipei (TW); Chuan-Yen Kao, New Taipei (TW); Tsung-Yin Tsou, New Taipei (TW)

(73) Assignee: Wistron Corporation, New Taipei (TW)

( * ) Notice: Subject to any disclaimer, the term of this patent is extended or adjusted under 35 U.S.C. 154(b) by 369 days.

(21) Appl. No.: 16/660,829

(22) Filed: Oct. 23, 2019

(65) Prior Publication Data
US 2021/0027599 A1  Jan. 28, 2021

(30) Foreign Application Priority Data

Jul. 23, 2019  (TW) .................................. 108125915

(51) Int. Cl.
*G08B 21/02* (2006.01)
*G08B 21/18* (2006.01)
(Continued)

(52) U.S. Cl.
CPC ............ *G08B 21/02* (2013.01); *A61B 5/1036* (2013.01); *A61B 5/1122* (2013.01); *A61B 5/4023* (2013.01); *A61B 5/6807* (2013.01); *A61B 5/746* (2013.01); *G08B 7/06* (2013.01); *G08B 21/182* (2013.01); *A61B 2562/0219* (2013.01); *A61B 2562/0247* (2013.01); *A61B 2562/046* (2013.01)

(58) Field of Classification Search
CPC ........ G08B 21/02; G08B 7/06; G08B 21/182; A61B 5/1036; A61B 5/1122; A61B 5/4023; A61B 5/6807; A61B 5/746; A61B 2562/0219; A61B 2562/0247; A61B 2562/046
USPC ........................................................ 702/139
See application file for complete search history.

(56) References Cited

U.S. PATENT DOCUMENTS 9,456,785 B1 * 10/2016 Matak ..................... G06F 17/00
2004/0140787 A1 * 7/2004 Okamoto ............... B25J 9/1612
318/568.21
(Continued)

FOREIGN PATENT DOCUMENTS

CN   106448057 A   2/2017
CN   109069066 A   12/2018
(Continued)

*Primary Examiner* — Zhen Y Wu
(74) *Attorney, Agent, or Firm* — Winston Hsu

(57) ABSTRACT

A wearable device and a method of operating the same are provided. The wearable device includes a shoe assembly, a plurality of pressure sensors, a processing circuit and an alarm module. The plurality of pressure sensors are disposed on the shoe assembly and configured to generate a plurality of pressure sensing values. The processing circuit is configured to calculate a center of gravity coordinate according to the plurality of pressure sensing values and coordinates of the plurality of pressure sensors, and generate a determination result according to the center of gravity coordinate. The alarm module is configured to output an alarm signal to perform an alarm function.

12 Claims, 9 Drawing Sheets

(51) Int. Cl.
  *G08B 7/06*   (2006.01)
  *A61B 5/103*  (2006.01)
  *A61B 5/00*   (2006.01)
  *A61B 5/11*   (2006.01)

(56) References Cited

U.S. PATENT DOCUMENTS

| | | | | |
|---|---|---|---|---|
| 2005/0165507 | A1* | 7/2005 | Shimizu | B62D 57/032 |
| | | | | 700/245 |
| 2009/0137933 | A1* | 5/2009 | Lieberman | A61B 5/1117 |
| | | | | 600/595 |
| 2009/0247909 | A1* | 10/2009 | Mukumoto | A61B 5/1036 |
| | | | | 600/592 |
| 2009/0260426 | A1* | 10/2009 | Lieberman | A61B 5/1118 |
| | | | | 73/65.01 |
| 2010/0292953 | A1* | 11/2010 | Pingel | G01B 11/22 |
| | | | | 702/138 |
| 2012/0253233 | A1* | 10/2012 | Greene | G16H 50/30 |
| | | | | 600/592 |
| 2014/0330171 | A1* | 11/2014 | Pan | A61B 5/1122 |
| | | | | 600/595 |
| 2015/0182844 | A1* | 7/2015 | Jang | A43B 3/34 |
| | | | | 177/4 |
| 2015/0351484 | A1* | 12/2015 | Rubin | A61B 5/1036 |
| | | | | 36/43 |
| 2015/0359457 | A1* | 12/2015 | Blumenthal | A61B 5/1038 |
| | | | | 73/172 |
| 2016/0157756 | A1* | 6/2016 | Yu | A61B 5/0024 |
| | | | | 600/595 |
| 2017/0225033 | A1* | 8/2017 | Czaja | A43B 5/00 |
| 2017/0241797 | A1* | 8/2017 | Kong | A61B 5/1123 |
| 2020/0035081 | A1* | 1/2020 | Pan | G08B 21/043 |

FOREIGN PATENT DOCUMENTS

| | | |
|---|---|---|
| JP | 2012-11136 A | 1/2012 |
| JP | 5747034 B2 | 7/2015 |
| JP | 5993574 B2 | 9/2016 |
| TW | 201346238 A | 11/2013 |

* cited by examiner

WEARABLE DEVICE AND METHOD OF OPERATING THE SAME

BACKGROUND OF THE INVENTION

1. Field of the Invention

The present invention relates to a wearable device and a method of operating the same, and more particularly, to a wearable device equipped with pressure sensors and inertial sensors and a method of operating the same.

2. Description of the Prior Art

The current exoskeleton robot can collect joint angles and postures of a user for determining the user's movement. However, since the current exoskeleton robot does not have components capable of contacting the ground and accurately predicting a center of gravity (COG). Therefore, it is unable to ensure whether the user has fallen. In addition, older people, younger people or patients are more likely to fall in daily life. Fall accidents often result in fractures, head trauma, or even death. Therefore, how to prevent falls and injuries become an important issue in the field.

SUMMARY OF THE INVENTION

Therefore, the present invention primarily provides a wearable device equipped with pressure sensors and inertial sensors, and a method of operating the same to solve the above mentioned problems.

According to an aspect of an embodiment, a wearable device includes a shoe assembly; a plurality of pressure sensors, disposed on the shoe assembly and configured to generate a plurality of pressure sensing values; a processing circuit, configured to calculate a center of gravity coordinate according to the plurality of pressure sensing values and coordinates of the plurality of pressure sensors and configured to generate a determination result according to the center of gravity coordinate; and an alarm module, configured to output an alarm signal to perform an alarm function according to the determination result.

According to an aspect of another embodiment, a method of operating a wearable device is disclosed. The wearable device includes a shoe assembly and a plurality of pressure sensors disposed on the shoe assembly. The method includes utilizing the plurality of pressure sensors to generate a plurality of pressure sensing values; calculating a center of gravity coordinate according to the plurality of pressure sensing values and coordinates of the plurality of pressure sensors and generating a determination result according to the center of gravity coordinate; and outputting an alarm signal to perform an alarm function according to the determination result.

These and other objectives of the present invention will no doubt become obvious to those of ordinary skill in the art after reading the following detailed description of the preferred embodiment that is illustrated in the various figures and drawings.

DETAILED DESCRIPTION

Certain terms are used throughout the description and following claims to refer to particular components. As one skilled in the art will appreciate, hardware manufacturers may refer to a component by different names. This document does not intend to distinguish between components that differ in name but not function. In the following description and in the claims, the terms "include" and "comprise" are utilized in an open-ended fashion, and thus should be interpreted to mean "include, but not limited to . . . ". Also, the term "couple" is intended to mean either an indirect or direct electrical connection. Accordingly, if one device is coupled to another device, that connection may be through a direct electrical connection, or through an indirect electrical connection via other devices and connections.

Figure 1:
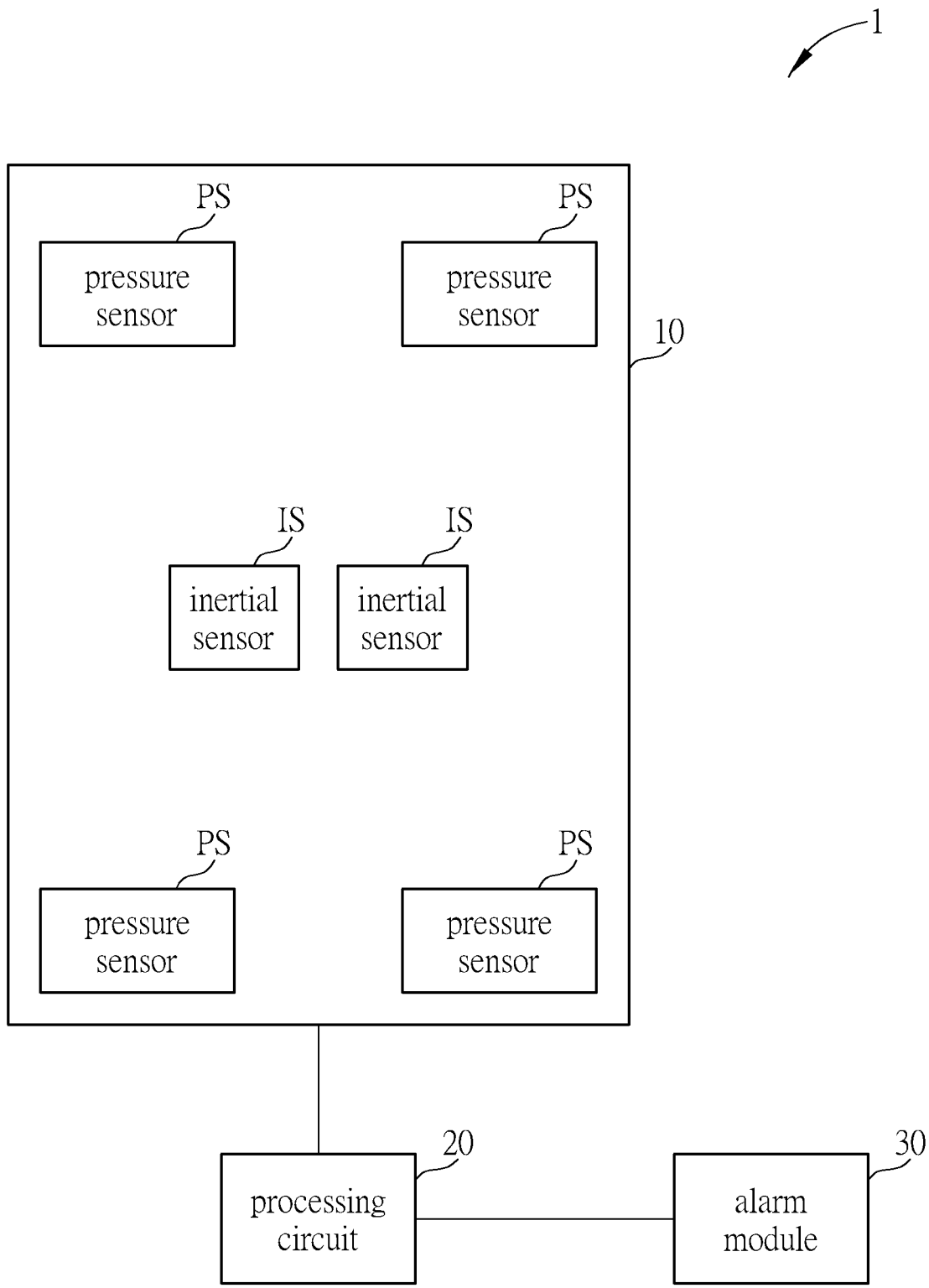
FIG. 1 is a schematic diagram illustrating a wearable device according to an embodiment of the present invention.

Please refer to FIG. 1, which is a schematic diagram illustrating a wearable device 1 according to an embodiment of the present invention. For example, the wearable device 1 can be applied to shoes, assistive devices, exoskeleton robots, socks, clothes, but not limited thereto. The wearable device 1 includes a shoe assembly 10, a processing circuit 20, an alarm module 30, pressure sensors PS and inertial sensors IS. The shoe assembly 10 can be outsoles, insoles, the bottom of an exoskeleton robot that contacts the ground) or any other device that can be worn on the feet. The processing circuit 20 can be a microprocessor control unit (MCU), a central processing unit (CPU) or a microprocessor, but not limited thereto. The alarm module 30 is configured to output an alarm signal for performing an alarm function. The alarm module 30 includes, but is not limited to, a light emitting device (e.g., light emitting diode (LED)), a speaker, a buzzer or a vibrator for generating the alarm signal (via all kinds of ways, e.g., sound, light or vibration) to inform the user.

The pressure sensors PS are disposed on the shoe assembly 10 and configured to sense and generate pressure sensing values. The pressure sensors PS include, but are not limited to, force sensitive resistors (FSRs), capacitive pressure sensors, piezoelectric pressure sensors or strain type pressure sensors. The inertial sensors IS are disposed on the shoe assembly 10 and configured to sense and generate displacement values (e.g., including moving direction and moving distance) and tilt angles. The inertial sensors IS may include, but are not limited to, accelerometers, gyroscopes and magnetometers. The inertial sensors IS can be inertial measurement units (IMUs). The number of the pressure sensors PS and the number of the inertial sensors IS are not limited, and may be varied and designed according to practical system demands. In addition, the wearable device 1 further includes an analog to digital converter (not shown in figures). The analog to digital converter can convert analog pressure sensing values sensed by the pressure sensors PS into digital pressure sensing values provided to the processing circuit 20. The analog to digital converter can also convert analog sensing values sensed by the inertial sensors IS into digital sensing values provided to the processing circuit 20.

Figure 2:
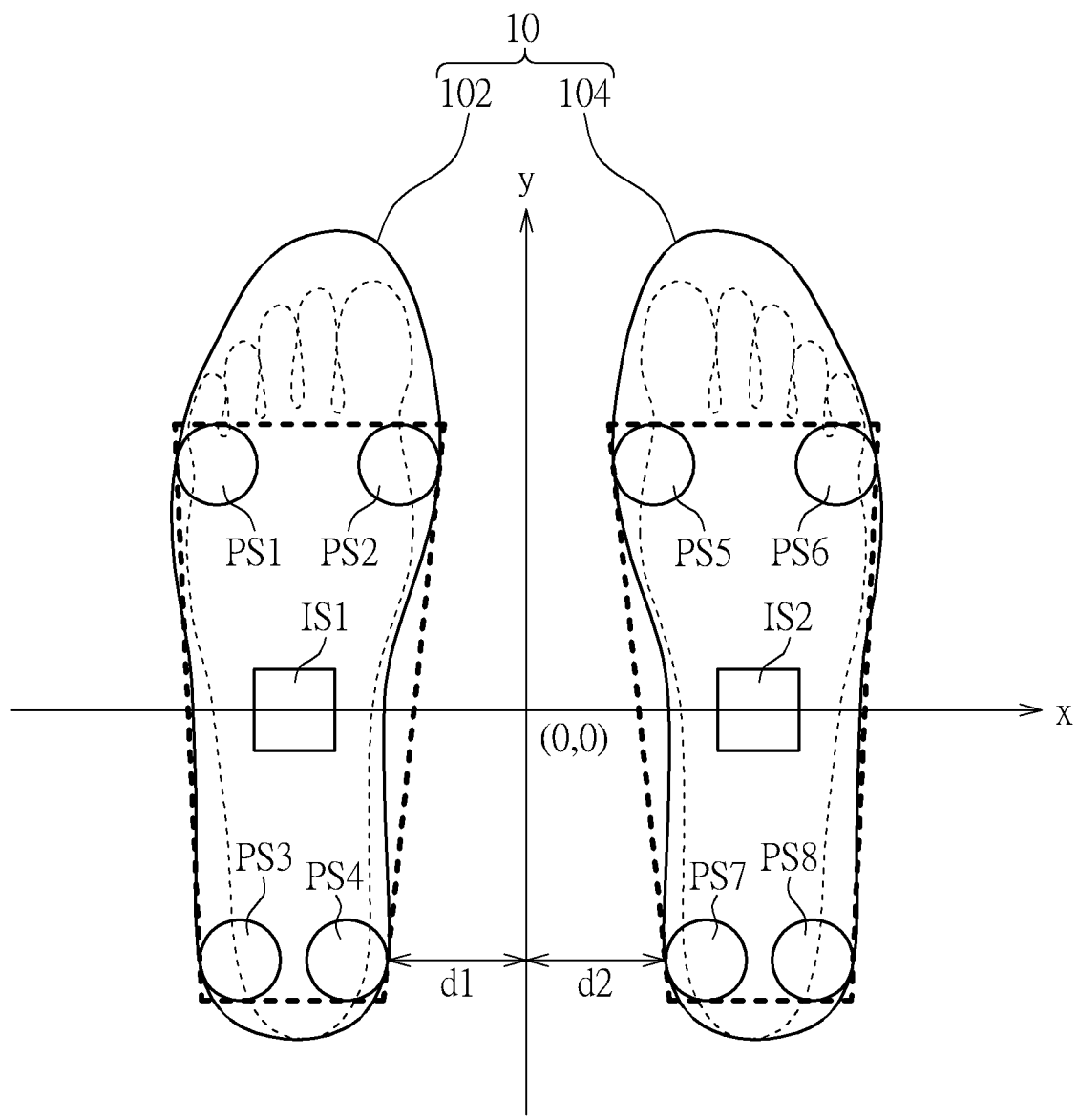
FIG. 2 is a schematic diagram illustrating a shoe assembly and pressure sensors shown in FIG. 1 according to an embodiment of the present invention.

For example, please refer to FIG. 2. FIG. 2 is a schematic diagram illustrating the shoe assembly 10 and the pressure sensors PS shown in FIG. 1 according to an embodiment of the present invention. As shown in FIG. 2, the shoe assembly 10 includes a left shoe assembly 102 and a right shoe assembly 104. For example, the left shoe assembly 102 is a left insole and the right shoe assembly 104 is a right insole. The pressure sensors PS1-PS4 are disposed on the left shoe assembly 102. The pressure sensors PS5-PS8 are disposed on the right shoe assembly 104. The pressure sensing value sensed by each pressure sensor can be transmitted to the processing circuit 20 for the following operation. Where (x1, y1), (x2, y2), (x3, y3), (x4, y4) represent the coordinates of the pressure sensors PS1-PS4, respectively. (X5, y5), (x6, y6), (x7, y7), (x8, y8) represent the coordinates of the pressure sensors PS5-PS8, respectively. D1 is the initial distance between the left foot and the y axis, d2 is the initial distance between the right foot and the y axis, and the distance between the user's feet can be represented as d1+d2 which can be used as the initial setting value.

Figure 3:
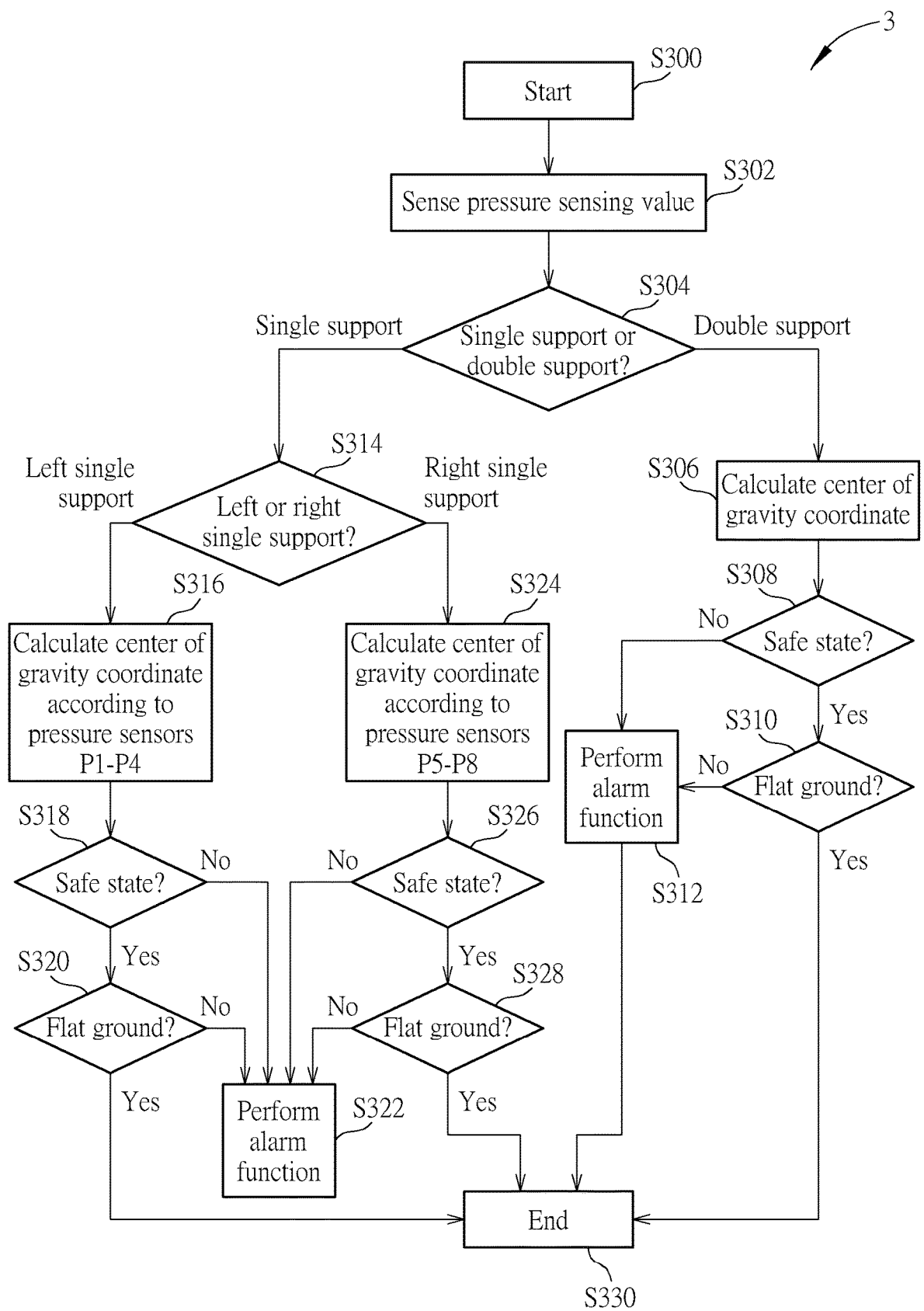
FIG. 3 is a flow diagram of a procedure according to an embodiment of the present invention.

For an illustration of the operations of the wearable device 1, please refer to FIG. 3. FIG. 3 is a flow diagram of a procedure 3 according to an embodiment of the present invention. The flowchart in FIG. 3 mainly corresponds to the operations on the wearable device 1 shown in FIG. 1 and FIG. 2. According to the procedure 3, in Step S302, when the user is wearing the wearable device 1 and the foot of the user is applying force on the pressure sensors, the pressure sensors disposed on the shoe assembly 10 are configure to sense and generate corresponding pressure sensing values. The pressure sensing value sensed by each pressure sensor can be transmitted to the processing circuit 20 through wireless or wired connections. The inertial sensors IS disposed on the shoe assembly 10 are configure to sense and generate the displacement values including moving direction and moving distance and the tilt angles, and these sensed values can be transmitted to the processing circuit 20 through wireless or wired connections.

In Step S304, the processing circuit 20 determines whether the user is standing on both feet (i.e. double support) or standing on one foot (i.e. single support). For example, the processing circuit 20 can determine whether the user is standing on both feet or standing on one foot according to the pressure sensing values sensed by the pressure sensors. For example, when the pressure sensing values sensed by the pressure sensors PS1-PS4 disposed on the left shoe assembly 102 and the pressure sensing values sensed by the pressure sensors PS5-PS8 disposed on the right shoe assembly 104 are greater than or equal to a threshold value, the processing circuit 20 determines that the user is standing on both feet. When the pressure sensing values sensed by the pressure sensors PS1-PS4 disposed on the left shoe assembly 102 (or the pressure sensing values sensed by the pressure sensors PS5-PS8 disposed on the right shoe assembly 104) are smaller than the threshold value, the processing circuit 20 determines that the user is standing on a single foot. For example, when a first percentage (e.g., 50%, 70%, but not limited thereto) of the pressure sensing values sensed by the pressure sensors PS1-PS4 disposed on the left shoe assembly 102 and the first percentage of the pressure sensing values sensed by the pressure sensors PS5-PS8 disposed on the right shoe assembly 104 are greater than or equal to the threshold value, the processing circuit 20 determines that the user is standing on both feet. When the first percentage of the pressure sensing values sensed by the pressure sensors PS1-PS4 disposed on the left shoe assembly 102 (or the first percentage of the pressure sensing values sensed by the pressure sensors PS5-PS8 disposed on the right shoe assembly 104) are smaller than the threshold value, the processing circuit 20 determines that the user is standing on a single foot.

When the processing circuit 20 determines that the user is standing on both feet (i.e. double support) in Step S304, then Step S306 is executed. In Step S306, the processing circuit 20 calculates a center of gravity (COG) coordinate according to the pressure sensing values sensed by the pressure sensors PS1-PS4 disposed on the left shoe assembly 102 and the pressure sensing values sensed by the pressure sensors PS5-PS8 disposed on the right shoe assembly 104. The COG coordinate may be calculated by the processing unit 20 according to the following equation:

$$COG(x_{COG}, y_{COG}) = \begin{cases} x_{COG} = \dfrac{\sum_{i=1}^{n} x_i P_i}{\sum_{i=1}^{n} P_i} \\ y_{COG} = \dfrac{\sum_{i=1}^{n} y_i P_i}{\sum_{i=1}^{n} P_i} \end{cases} \quad (1)$$

where $COG(X_{COG}, Y_{COG})$ represents the COG coordinate, $X_{COG}$ represents an x-axis coordinate value of the COG coordinate, $Y_{COG}$ represents a y-axis coordinate value of the COG coordinate, $x_i$ represents the x-axis coordinate value of i-th pressure sensor (e.g., pressure sensor $PS_i$), $P_i$ represents the pressure sensing value of i-th pressure sensor (e.g., pressure sensor $PS_i$), $y_i$ represents the y-axis coordinate value of i-th pressure sensor (e.g., pressure sensor $PS_i$), and n represents the number of the pressure sensors. For example, when the processing circuit calculates a COG coordinate according to the pressure sensing values sensed by the pressure sensors PS1-PS4 disposed on the left shoe assembly 102 and the pressure sensing values sensed by the pressure sensors PS5-PS8 disposed on the right shoe assembly 104. In such a situation, n is 8.

Figure 4:
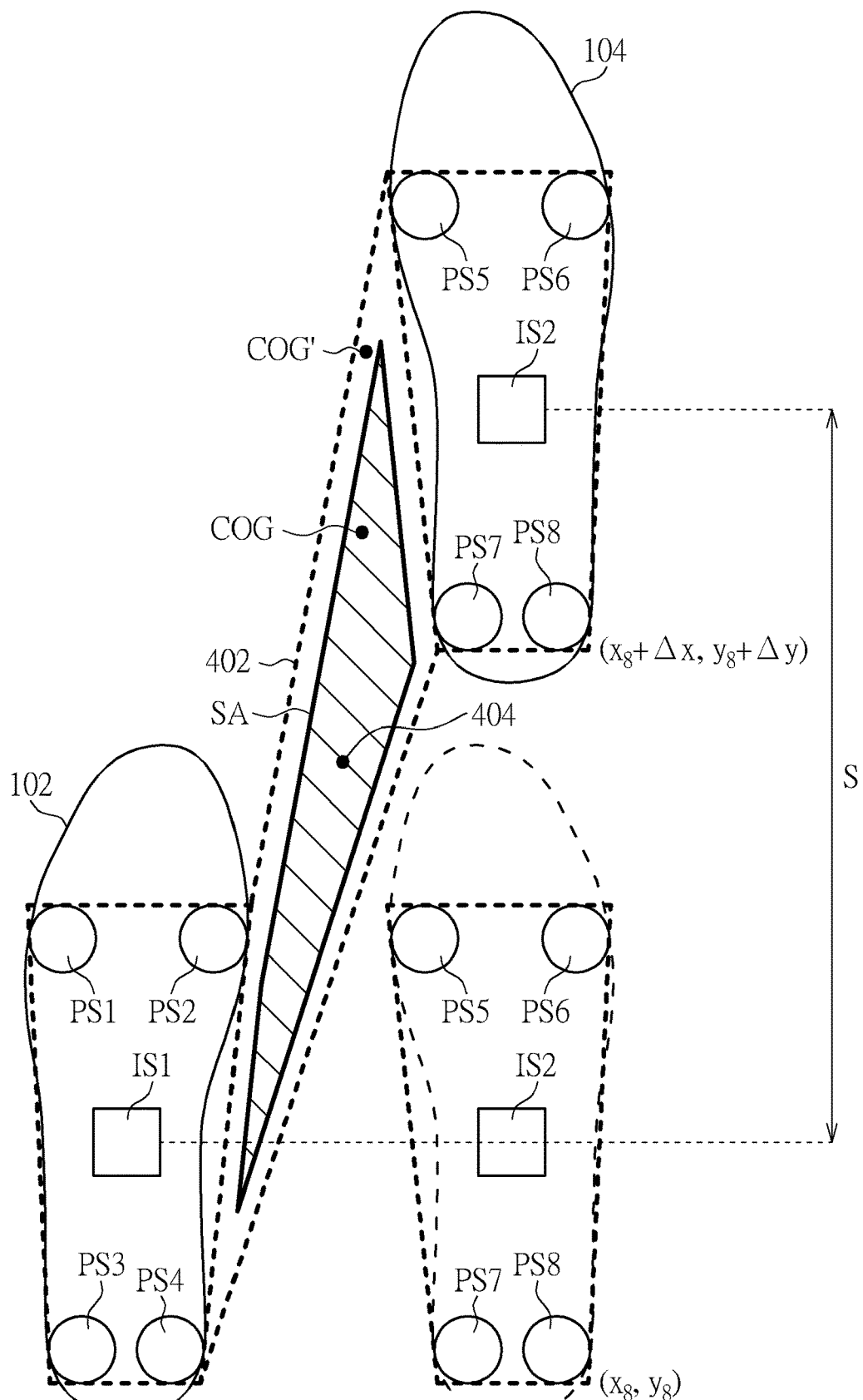
FIG. 4 is a schematic diagram illustrating center of gravity coordinates and a safety area according to an embodiment of the present invention.

In Step S308, the processing circuit 20 determines whether the user is in a safe state to generate a determination result according to the calculated COG coordinate. For example, the processing circuit 20 can determine whether COG coordinate calculated in Step S306 is located within a safety area SA. For example, the safety area SA can be an area between the left shoe assembly 102 and the right shoe assembly 104. For example, the safety area SA is within an area formed by pressure sensors disposed inside the left shoe assembly 102 (e.g., pressure sensors disposed on the left shoe assembly 102 and approaching the right shoe assembly 104) and pressure sensors disposed inside the right shoe assembly 104 (e.g., pressure sensors disposed on the right shoe assembly 104 and approaching the left shoe assembly 102). For example, as shown in FIG. 4, the pressure sensors PS2, PS4, PS5 and PS7 form an area 402. The safety area SA is in the area 402 formed by the pressure sensors PS2, PS4, PS5 and PS7. Moreover, the safety area SA can be an area extending outward from a reference point between the left shoe assembly 102 and the right shoe assembly 104. For example, as shown in FIG. 4, if a reference point 404 is a center point of the pressure sensors PS2, PS4, PS5 and PS7. The safety area SA is an area extending outward from the reference point 404. The area size of the safety area SA can be adjusted by the user. The level of the security alarm can be determined by adjusting the area size of the safety area SA according to different requirements. The processing circuit 20 can determine whether the COG coordinate calculated in Step S306 is located within the safety area SA. In an embodiment, if a COG coordinate COG is calculated by the processing circuit 20 according to the current coordinates of the pressure sensors PS1-PS8, pressure sensing values sensed by the pressure sensors PS1-PS8 and equation (1). As shown in FIG. 4, the COG coordinate COG is in the safety area SA, this means that the user is walking with firm and steady steps. As such, the processing circuit 20 determines that the user is in the safe state and generates the determination result indicating that the user is in the safe state. Further, Step S310 is executed.

Figure 5:
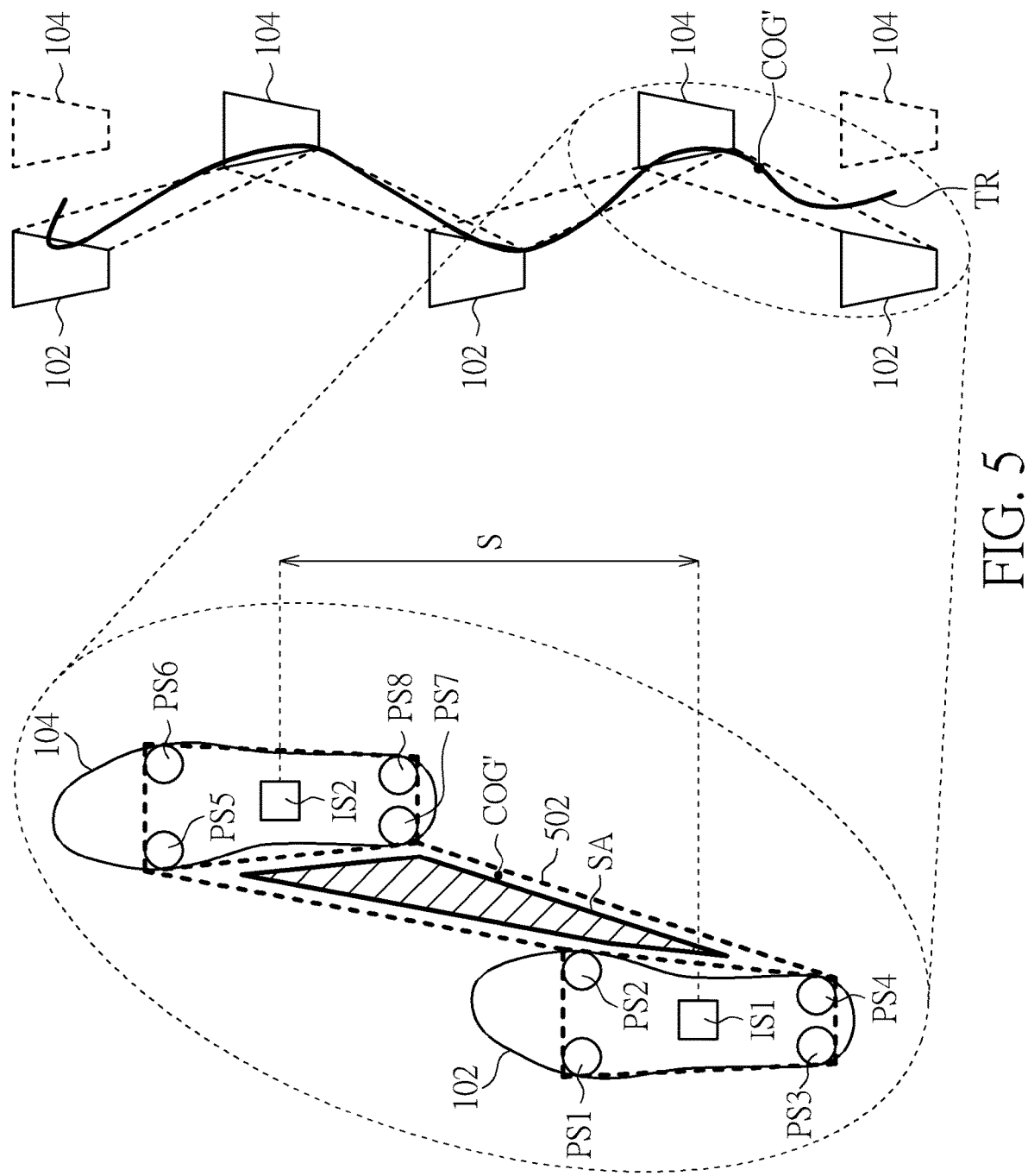
FIG. 5 is a schematic diagram illustrating a trajectory of the center of gravity coordinate according to an embodiment of the present invention.

Please further refer to FIG. 4, if a COG coordinate COG' is calculated by the processing circuit 20 according to the current coordinates of the pressure sensors PS1-PS8, pressure sensing values sensed by the pressure sensors PS1-PS8 and equation (1). As shown in FIG. 4, the COG coordinate COG' is not in the safety area SA. This means that the COG coordinate COG' is located outside the safety area SA and the user may have lost his/her balance and be at risk of falling. As such, the processing circuit 20 determines that the user is in an unsafe state and accordingly generates the determination result indicating that the user is in the unsafe state. In more detail, please refer to FIG. 5. FIG. 5 is a schematic diagram illustrating a trajectory of a COG coordinate according to an embodiment of the present invention. As shown in FIG. 5, the safety area SA is in the area 502 formed by the pressure sensors PS2, PS4, PS5 and PS7. As the user walks forward, a trajectory TR of the COG coordinate is shown in FIG. 5. At a first time point, a COG coordinate COG' is calculated by the processing circuit 20 according to the current coordinates of the pressure sensors PS1-PS8, pressure sensing values sensed by the pressure sensors PS1-PS8 and equation (1). As shown in FIG. 5, the COG coordinate COG' is not in the safety area SA. In such a situation, the processing circuit 20 determines that the user is in an unsafe state. The processing circuit 20 generates the determination result indicating that the user is in the unsafe state. Further, Step S312 is executed. In other words, the processing circuit 20 can simultaneously detect whether the user is in the safe state during movement.

In addition, the coordinate of the pressure sensor can be updated according to the displacement values in the horizontal direction (x-y plane) sensed by the inertial sensor. For example, please further refer to FIG. 4, the coordinate of the pressure sensor PS8 at a first time point is represented as (x8, y8). A displacement value Δx in the x axis direction between the first time point and a second time point is sensed by the inertial sensor IS2. A displacement value Δy in the y axis direction between the first time point and the second time point is sensed by the inertial sensor IS2. As such, the coordinate of the pressure sensor PS8 at the second time point is represented as (x8+Δx, y8+Δy), and so on.

On the other hand, in Step S308, the processing circuit 20 can calculate a predicted COG coordinate according to a previous calculated COG coordinate and a current calculated COG coordinate and determine whether the predicted COG coordinate is located within the safety area SA. For example, the processing circuit 20 can calculate a movement speed moving from the previous calculated COG coordinate to the current calculated COG coordinate according to a distance between the previous calculated COG coordinate and the current calculated COG coordinate and movement time. The processing circuit 20 can calculate a predicted COG coordinate of the next time point according to the calculated movement speed and a movement direction from the previous calculated COG coordinate to the current calculated COG coordinate. For example, the processing circuit 20 calculates a COG coordinate COG(t−1) of the time point t−1 according to the coordinates of the pressure sensors PS1-PS8 at the time point t−1, the pressure sensing values sensed by the pressure sensors PS1-PS8 at the time point t−1 and equation (1). The processing circuit 20 calculates a COG coordinate COG(t) of the time point t according to the coordinates of the pressure sensors PS1-PS8 at the time point t, the pressure sensing values sensed by the pressure sensors PS1-PS8 at the time point t and equation (1). The processing circuit 20 calculates a distance between the COG coordinate COG(t−1) and the COG coordinate COG(t) and calculates a movement speed of the COG coordinate by dividing the calculated distance by the time difference between the time point t and the time point t−1. The processing circuit 20 calculates a predicted movement distance by multiplying the calculated movement speed of the COG coordinate with the time difference between the time point t+1 and the time point t. The processing circuit 20 calculates a predicted COG coordinate of the time point t+1 according to the calculated predicted movement distance and a movement direction from the COG coordinate COG(t−1) to the COG coordinate COG(t). After that, the processing circuit 20 can determine whether the calculated predicted COG coordinate is located within the safety area SA. When determining that the calculated predicted COG coordinate is located within the safety area SA, this means that the user will be in a safe state. When determining that the calculated predicted COG coordinate is located outside the safety area SA, this means that the user will be in an unsafe state. The processing circuit 20 generates the determination result indicating that the user will be in an unsafe state.

Figure 6:
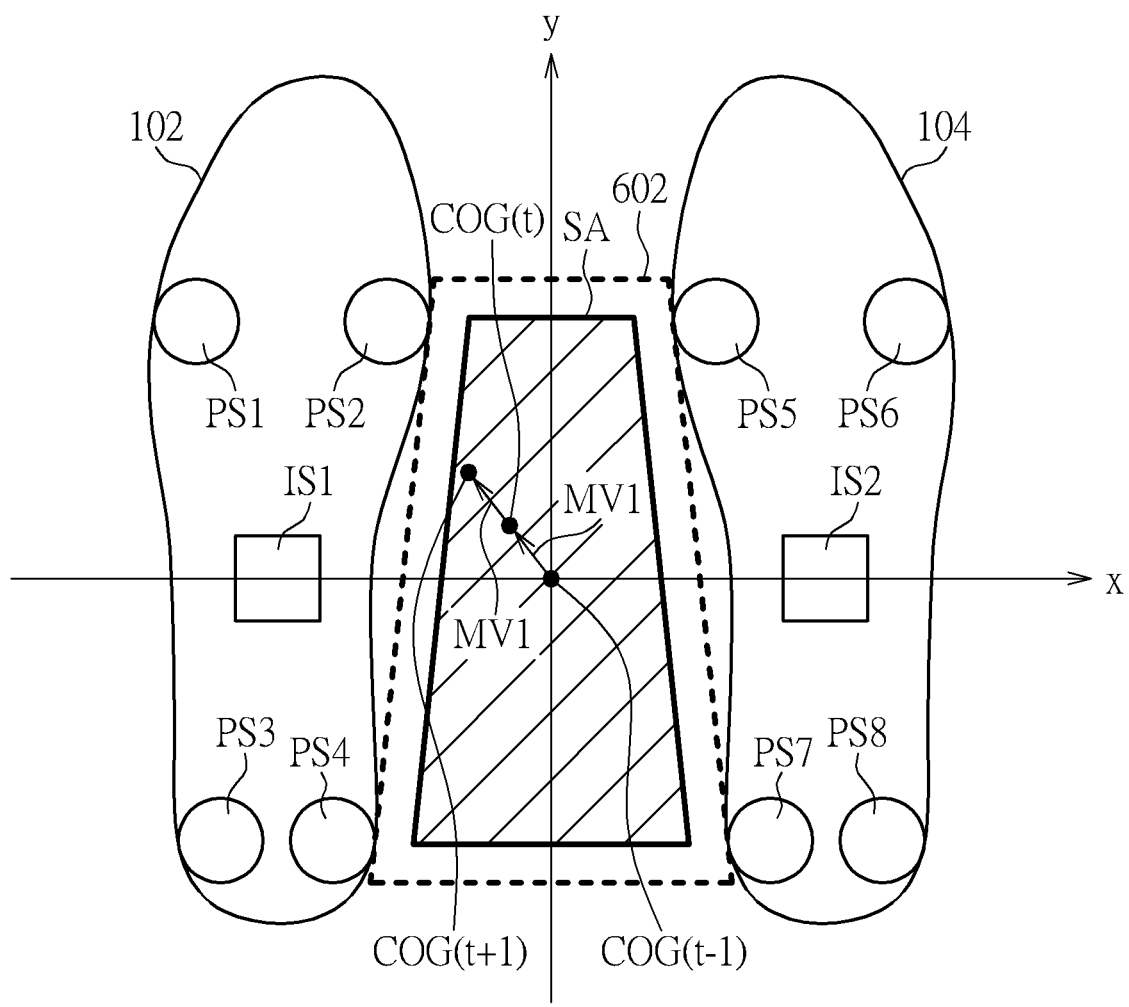
FIG. 6 and FIG. 7 are schematic diagrams illustrating the center of gravity coordinates and the safety area according to alternative embodiments of the present invention.

For example, please refer to FIG. 6. Suppose the time difference between the time point t and the time point t−1 is equal to the time difference between the time point t+1 and the time point t. The processing circuit 20 calculates the movement speed and the movement direction of the COG coordinate according to the COG coordinate COG(t−1) of the time point t−1 and the COG coordinate COG(t) of the time point t. The processing circuit 20 calculates a vector MV1 by subtracting the COG coordinate COG(t−1) of the time point t−1 from the COG coordinate COG(t) of the time point t. The vector MV1 includes the distance between the COG coordinate COG(t−1) of the time point t−1 and the COG coordinate COG(t) of the time point t and the movement direction from the COG coordinate COG(t−1) of the time point t−1 to the COG coordinate COG(t) of the time point t. The processing circuit 20 calculates a predicted COG coordinate COG(t+1) by adding the vector MV1 to the COG coordinate COG(t). As shown in FIG. 6, the safety area SA is in the area 602 formed by the pressure sensors PS2, PS4, PS5 and PS7. The calculated predicted COG coordinate COG(t+1) is located within the safety area SA, this means that the user will be in a safe state at the next time point. After that, Step S310 is executed.

Figure 7:
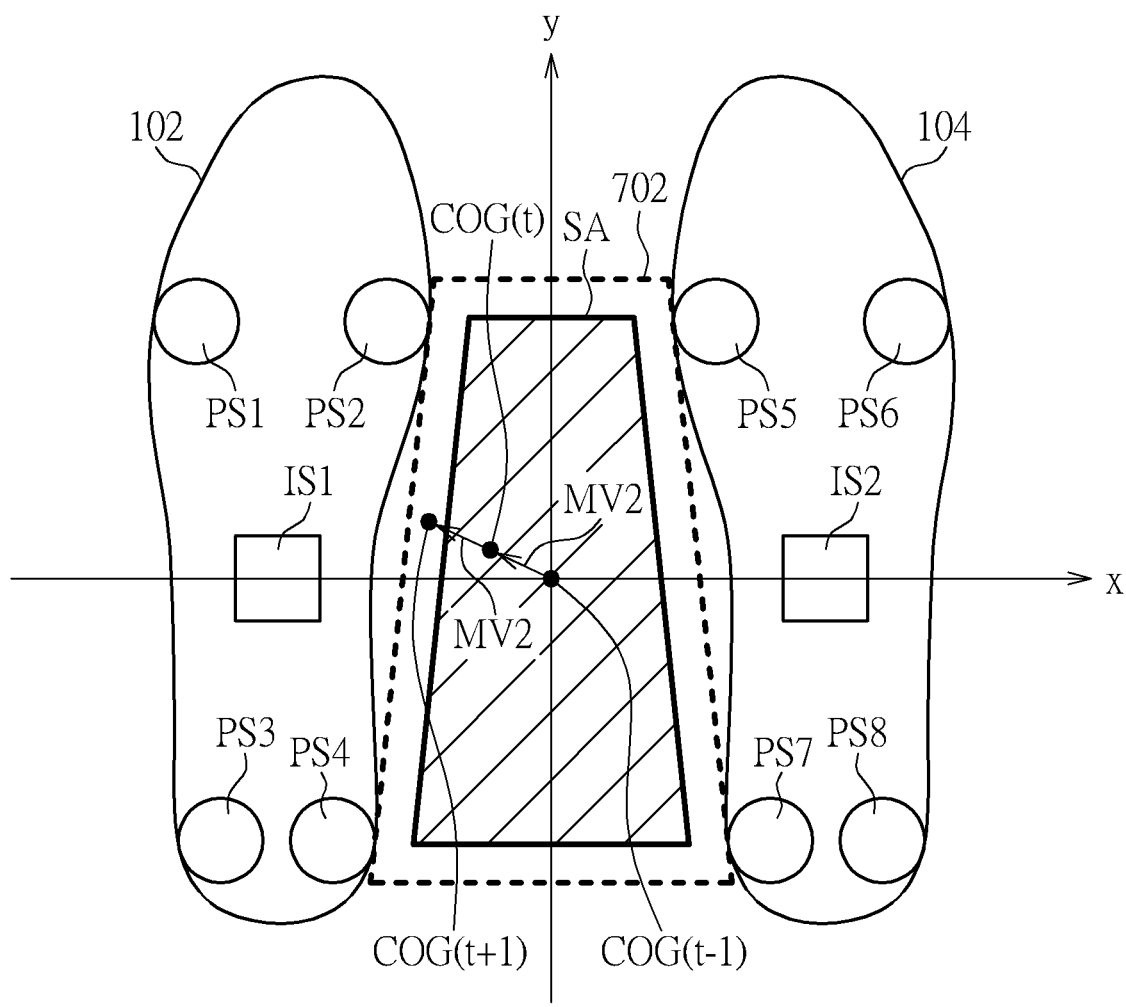

For example, please refer to FIG. 7. Suppose the time difference between the time point t and the time point t−1 is equal to the time difference between the time point t+1 and the time point t. The processing circuit 20 calculates the movement speed and the movement direction of the COG coordinate according to the COG coordinate COG(t−1) of the time point t−1 and the COG coordinate COG(t) of the time point t. The processing circuit 20 calculates a vector MV2 by subtracting the COG coordinate COG(t−1) of the time point t−1 from the COG coordinate COG(t) of the time point t. The processing circuit 20 calculates a predicted COG coordinate COG(t+1) by adding the vector MV2 to the COG coordinate COG(t). As shown in FIG. 7, the safety area SA is in the area 702 formed by the pressure sensors PS2, PS4, PS5 and PS7. The calculated predicted COG coordinate COG(t+1) is located outside the safety area SA, this means that the user will be in an unsafe state at the next time point. After that, Step S312 is executed.

In Step S310, each inertial sensor is configured to sense a tilt angle with respect to the horizontal plane. The processing circuit 20 compares the tilt angle sensed by the each inertial sensor with a first threshold angle value for determining whether the user is standing on a flat ground or a slope ground. The first threshold angle value can be an angle of repose or a critical angle of repose, but not limited thereto. In an embodiment, the inertial sensors IS1 and IS2 shown in FIG. 2 are configured to sense tilt angles with respect to the horizontal plane, respectively. When the tilt angles sensed by the inertial sensors IS1 and IS2 are greater than or equal to the first threshold angle value, this means the user may be standing on a slope ground. Then, Step S312 is executed and the alarm module 30 outputs an alarm signal to notify that the user is in an unsafe state. When the tilt angles sensed by the inertial sensors IS1 and IS2 are smaller than the first threshold angle value, this means the user may be standing on a flat ground. In an alternative embodiment, the inertial sensors IS1 and IS2 shown in FIG. 2 are configured to sense tilt angles with respect to the horizontal plane, respectively. When the tilt angle sensed by the inertial sensor IS1 or the tilt angle sensed by the inertial sensor IS2 is greater than or equal to the first threshold angle value, this means the user may be standing on a slope ground. Step S312 is then executed and the alarm module 30 outputs an alarm signal to notify that the user is in an unsafe state. When the tilt angles sensed by the inertial sensors IS1 and IS2 are smaller than the first threshold angle value, this means the user may be standing on a flat ground. In other words, since the inertial sensors IS1 and IS2 are disposed on the shoe assembly 10 and the user is wearing the wearable device 1, the processing circuit 20 can determine whether the user is standing on a flat ground or a slope ground according to the tilt angles sensed by the inertial sensors IS1 and IS2 and accordingly the alarm module 30 outputs the alarm signal for allowing the user to be aware that a fall event will occur and to take action to prevent falls.

In Step S312, the alarm module 30 outputs an alarm signal for performing an alarm function according to the determination result of Step S308 or Step S310. When the determination result of Step S308 or Step S310 indicates that the user is in the unsafe state or the user will be in an unsafe state, the alarm module 30 outputs the alarm signal to notify that the user is in an unsafe state and a fall event will occur for performing an alarm function. As such, through notification of the alarm signal, the user can immediately understand and be aware that a fall event will occur and take action to prevent falls. In brief, through notification of the alarm module 30, the user can easily and immediately obtain a fall prediction alarm to avoid a fall accident. In addition, when the determination result of Step S308 or Step S310 indicates that the user is in the unsafe state or the user will be in an unsafe state, the processing circuit 20 can also send notification signal to the external device, so that the external device generates alarm signals or performs related fall alarm functions.

When the processing circuit 20 determines that the user is standing on one foot (i.e. single support) in step S304, then Step S314 is executed. In Step S314, the processing circuit determines whether the user is standing on his/her left foot or right foot. For example, the processing circuit 20 can determine whether the user is standing on his/her left foot or right foot according to the pressure sensing values sensed by the pressure sensors. For example, when the pressure sensing values sensed by the pressure sensors PS1-PS4 disposed on the left shoe assembly 102 are smaller than the threshold value, the processing circuit 20 determines that the user is standing on his/her right foot (i.e. right single support). When the pressure sensing values sensed by the pressure sensors PS5-PS8 disposed on the right shoe assembly 104 are smaller than the threshold value, the processing circuit 20 determines that the user is standing on his/her left foot (i.e. left single support). For example, when a first percentage of the pressure sensing values sensed by the pressure sensors PS1-PS4 disposed on the left shoe assembly 102 are smaller than the threshold value, the processing circuit 20 determines that the user is standing on his/her right foot (i.e. right single support). When a first percentage of the pressure sensing values sensed by the pressure sensors PS5-PS8 disposed on the right shoe assembly 104 are smaller than the threshold value, the processing circuit 20 determines that the user is standing on his/her left foot (i.e. left single support).

When the processing circuit 20 determines that the user is standing on his/her left foot (i.e. left single support) in Step S314, and then Step S316 is executed. In Step S316, the processing circuit 20 calculates a COG coordinate according to the pressure sensing values sensed by the pressure sensors PS1-PS4 disposed on the left shoe assembly 102. In an embodiment, the processing circuit 20 divides the pressure sensors PS1-PS4 into a first group of pressure sensors and a second group of pressure sensors. Compared with the second group of pressure sensors, the first group of pressure sensors has larger pressure sensing values than the second group of pressure sensors. That is, the sensing value sensed by each of the first group of pressure sensors is greater than the sensing value sensed by each of the second group of pressure sensor. The processing circuit 20 calculates a COG coordinate of the first group of pressure sensors according to the coordinates of the first group of the pressure sensors, pressure sensing values sensed by the first group of the pressure sensors and equation (1). The processing circuit 20 calculates a COG coordinate of the second group of pressure sensors according to the coordinates of the second group of the pressure sensors, pressure sensing values sensed by the second group of the pressure sensors and equation (1). The processing circuit 20 calculates a trend vector of COG by subtracting the COG coordinate of the second group of pressure sensors from the COG coordinate of the first group of pressure sensors. In addition, the inertial sensor IS2 disposed on the right shoe assembly 104 senses a movement direction on the horizontal x-y plane.

Figure 8:
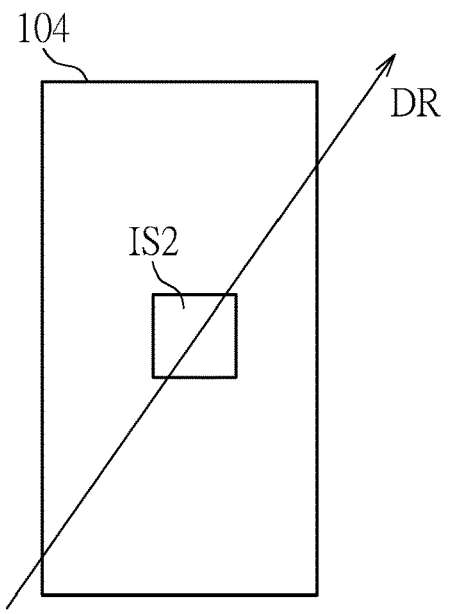
FIG. 8 is a schematic diagram illustrating a trend vector of the center of gravity coordinate and the movement direction according to an embodiment of the present invention.
Figure 8:
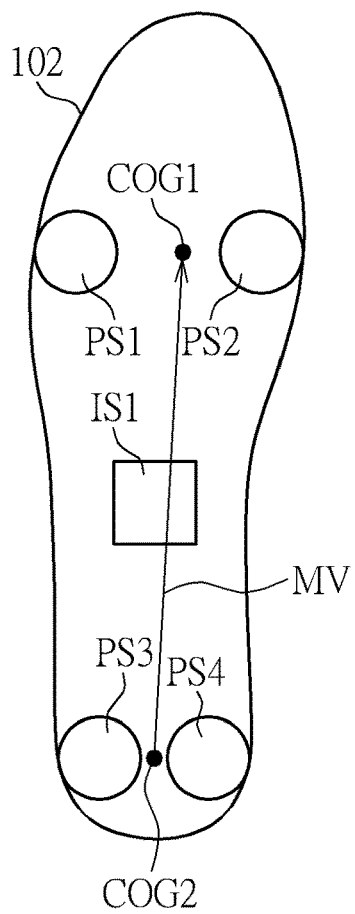
Figure 8:
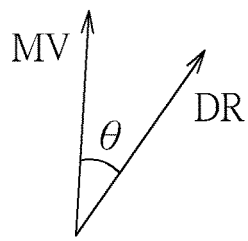

For example, please refer to FIG. 8. Suppose the pressure sensing value sensed by the pressure sensor PS1 is P1. The pressure sensing value sensed by the pressure sensor PS2 is P2. The pressure sensing value sensed by the pressure sensor PS3 is P3. The pressure sensing value sensed by the pressure sensor PS4 is P4. The relationship of the pressure sensing values PS1-PS4 is represented as followings: P2>P1>P4>P3. The pressure sensors PS1 and PS2 are set as the first group of pressure sensors by the processing circuit 20. The pressure sensors PS3 and PS4 are set as the second group of pressure sensors by the processing circuit 20. As shown in FIG. 8, the processing circuit 20 calculates a COG coordinate COG1 of the first group of pressure sensors according to the coordinates of pressure sensors PS1 and PS2, pressure sensing values sensed by the pressure sensors PS1 and PS2 and equation (1) and calculates a COG coordinate COG2 of the second group of pressure sensors according to the coordinates of pressure sensors PS3 and PS4, pressure sensing values sensed by the pressure sensors PS3 and PS4 and equation (1). The vector MV represents the trend vector of the COG. The inertial sensor IS2 disposed on the right shoe assembly 104 senses a movement direction DR.

Moreover, in Step S318, the processing circuit 20 compares the calculated trend vector of COG with the movement direction sensed by the inertial sensor IS2. The processing circuit 20 determines whether an angle between a direction of the calculated trend vector of the COG and the movement direction sensed by the inertial sensor IS2 is greater than or equal to a second threshold angle value. The angle between the direction of the calculated trend vector of COG and the movement direction sensed by the inertial sensor IS2 can be an inferior angle which is between 0 and 180 degrees. When the angle between the direction of the calculated trend vector of COG and the movement direction sensed by the inertial sensor IS2 is greater than or equal to the second threshold angle value, this means that the COG of the left foot of the user is significantly different from the movement direction of the right foot of the user. Accordingly, the processing circuit 20 determines that the user is in an unsafe state and accordingly generates the determination result indicating that the user is in the unsafe state. As shown in FIG. 8, when an angle θ between the direction of the calculated trend vector MV of the COG and the movement direction DR sensed by the inertial sensor IS2 is greater than or equal to the second threshold angle value, the processing circuit 20 determines that the user is in the unsafe state accordingly and Step S322 is then executed. When the angle between the direction of the calculated trend vector of COG and the movement direction sensed by the inertial sensor IS2 is smaller than the second threshold angle value, the processing circuit 20 determines that the user is in a safe state accordingly. As shown in FIG. 8, when the angle θ between the direction of the calculated trend vector MV of the COG and the movement direction DR sensed by the inertial sensor IS2 is smaller than the second threshold angle value, the processing circuit 20 determines that the user is in the safe state and Step S320 is then executed.

In an alternative embodiment, in Step S316, the processing circuit calculates a COG coordinate according to the pressure sensing values sensed by the pressure sensors PS1-PS4 disposed on the left shoe assembly 102. The processing circuit 20 calculates a COG coordinate COG(t-1) of the time point t-1 according to the coordinates of the pressure sensors PS1-PS4 at the time point t-1, the pressure sensing values sensed by the pressure sensors PS1-PS4 at the time point t-1 and equation (1). The processing circuit 20 calculates a COG coordinate COG(t) of the time point t according to the coordinates of the pressure sensors PS1-PS4 at the time point t, the pressure sensing values sensed by the pressure sensors PS1-PS4 at the time point t and equation (1). The processing circuit 20 calculates a COG movement vector by subtracting the COG coordinate COG(t-1) of the time point t-1 from the COG coordinate COG(t) of the time point t. In addition, the inertial sensor IS2 disposed on the right shoe assembly 104 senses a movement direction on the horizontal x-y plane. For example, please refer to FIG. 9. COG(t-1) represents the COG coordinate of the time point t-1. COG(t) represents the COG coordinate of the time point t. MV3 represents the COG movement vector. DR represents the movement direction sensed by the inertial sensor IS2.

Figure 9:
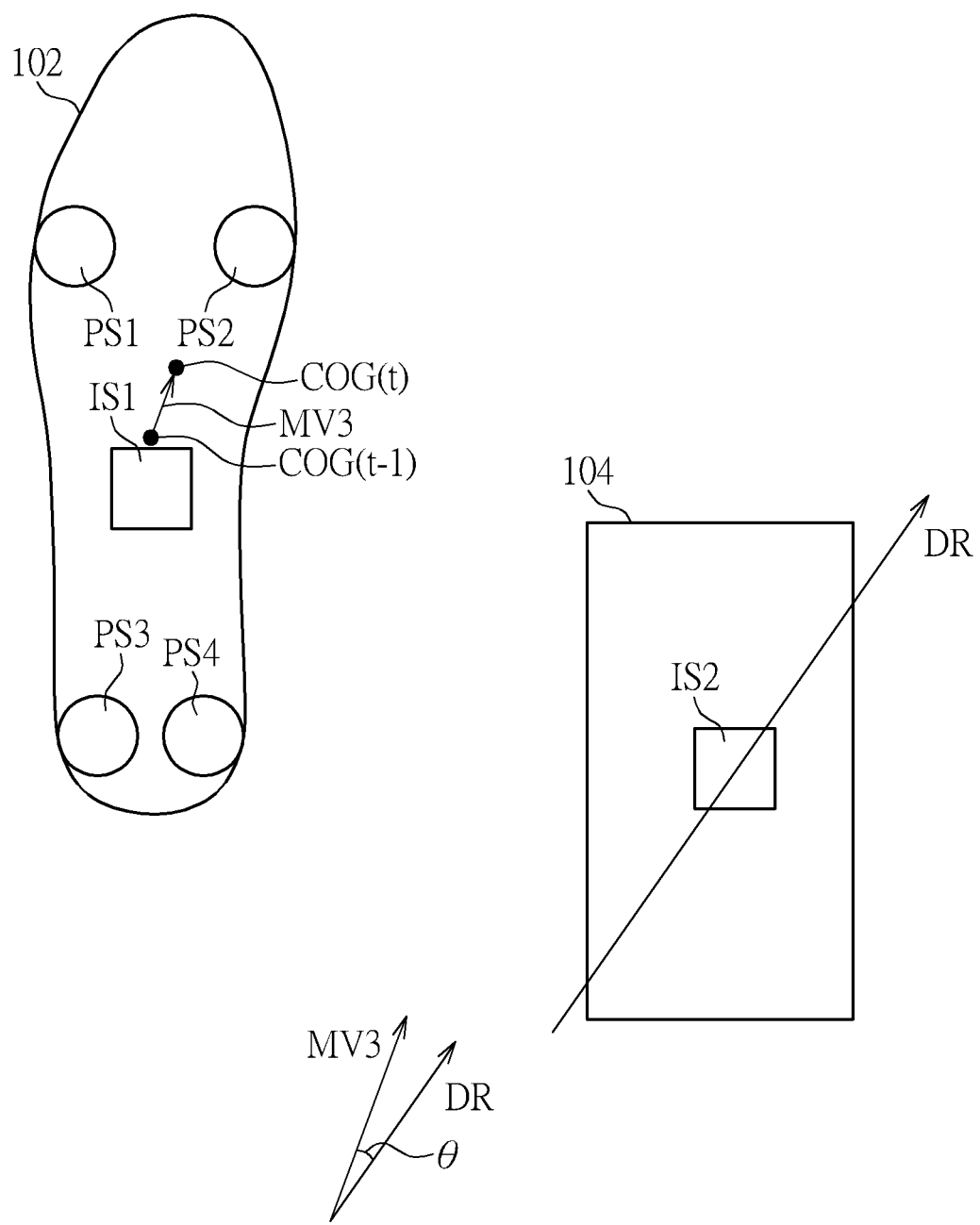
FIG. 9 is a schematic diagram illustrating the movement direction of the center of gravity and the movement direction of the inertial sensor according to an embodiment of the present invention.

Moreover, in Step S318, the processing circuit 20 compares the calculated COG movement vector with the movement direction sensed by the inertial sensor IS2. The processing circuit 20 determines whether an angle between a direction of the calculated COG movement vector and the movement direction sensed by the inertial sensor IS2 is greater than or equal to a third threshold angle value. The angle between the direction of the calculated COG movement vector and the movement direction sensed by the inertial sensor IS2 can be an inferior angle which is between 0 and 180 degrees. When the angle between the direction of the calculated COG movement vector and the movement direction sensed by the inertial sensor IS2 is greater than or equal to the third threshold angle value, this means that the COG variation of the left foot of the user is significantly different from the movement direction of the right foot of the user. Accordingly, the processing circuit 20 determines that the user is in an unsafe state and accordingly generates the determination result indicating that the user is in the unsafe state. As shown in FIG. 9, when an angle θ between the direction of the calculated COG movement vector MV3 and the movement direction DR sensed by the inertial sensor IS2 is greater than or equal to the third threshold angle value, the processing circuit 20 determines that the user is in the unsafe state accordingly and Step S322 is then executed. When the angle between the direction of the calculated COG movement vector MV3 and the movement direction sensed by the inertial sensor IS2 is smaller than the second threshold angle value, the processing circuit 20 determines that the user is in a safe state accordingly. As shown in FIG. 9, when the angle θ between the direction of the calculated COG movement vector and the movement direction DR sensed by the inertial sensor IS2 is smaller than the second threshold angle value, the processing circuit 20 determines that the user is in the safe state and Step S320 is then executed.

In Step S320, the inertial sensor IS1 disposed on the left shoe assembly 102 is configured to sense a tilt angle with respect to the horizontal plane. The processing circuit 20 compares the tilt angle sensed by the inertial sensor IS1 with a first threshold angle value for determining whether the user is standing on a flat ground or a slope ground. The first threshold angle value can be an angle of repose or a critical angle of repose, but not limited thereto. In an embodiment, the inertial sensor IS1 shown in FIG. 2 is configured to sense a tilt angle with respect to the horizontal plane. When the tilt angle sensed by the inertial sensor IS1 is greater than or equal to the first threshold angle value, this means the user may be standing on a slope ground. Step S322 is then executed and the alarm module 30 outputs an alarm signal to notify that the user is in an unsafe state. When the tilt angle sensed by the inertial sensor IS1 are smaller than the first threshold angle value, this means the user may be standing on a flat ground.

When the processing circuit 20 determines that the user is standing on his/her right foot (i.e. right single support) in Step S314, and then Step S324 is executed. Similar to Step S316, in Step S324, the processing circuit 20 calculates a COG coordinate according to the pressure sensing values sensed by the pressure sensors PS5-PS8 disposed on the right shoe assembly 104. In an embodiment, the processing circuit 20 divides the pressure sensors PS5-PS8 into a first group of pressure sensors and a second group of pressure sensors. Compared with the second group of pressure sensors, the first group of pressure sensors has larger pressure sensing values than the second group of pressure sensors. That is, the sensing value sensed by each of the first group of pressure sensors is greater than the sensing value sensed by each of the second group of pressure sensor. Further, the processing circuit 20 calculates a COG coordinate of the first group of pressure sensors according to the coordinates of the first group of the pressure sensors, pressure sensing values sensed by the first group of the pressure sensors and equation (1). The processing circuit 20 calculates a COG coordinate of the second group of pressure sensors according to the coordinates of the second group of the pressure sensors, pressure sensing values sensed by the second group of the pressure sensors and equation (1). The processing circuit 20 calculates a trend vector of COG by subtracting the COG coordinate of the second group of pressure sensors from the COG coordinate of the first group of pressure sensors. In addition, the inertial sensor IS1 disposed on the left shoe assembly 102 senses a movement direction on the horizontal x-y plane.

Moreover, in Step S326, the processing circuit 20 compares the calculated trend vector of COG with the movement direction sensed by the inertial sensor IS1. The processing circuit 20 determines whether an angle between a direction of the calculated trend vector of the COG and the movement direction sensed by the inertial sensor IS1 is greater than or equal to a second threshold angle value. The angle between the direction of the calculated trend vector of COG and the movement direction sensed by the inertial sensor IS1 can be an inferior angle which is between 0 and 180 degrees. When the angle between the direction of the calculated trend vector of COG and the movement direction sensed by the inertial sensor IS1 is greater than or equal to the second threshold angle value, the processing circuit 20 determines that the user is in an unsafe state and accordingly generates the determination result indicating that the user is in the unsafe state. Then, Step S322 is executed. When the angle between the direction of the calculated trend vector of COG and the movement direction sensed by the inertial sensor IS1 is smaller than the second threshold angle value, the processing circuit 20 determines that the user is in a safe state accordingly and Step S328 is then executed.

In an alternative embodiment, in Step S324, the processing circuit calculates a COG coordinate according to the pressure sensing values sensed by the pressure sensors PS5-PS8 disposed on the right shoe assembly 104. The processing circuit 20 calculates a COG coordinate COG(t−1) of the time point t−1 according to the coordinates of the pressure sensors PS5-PS8 at the time point t−1, the pressure sensing values sensed by the pressure sensors PS5-PS8 at the time point t−1 and equation (1). The processing circuit 20 calculates a COG coordinate COG(t) of the time point t according to the coordinates of the pressure sensors PS5-PS8 at the time point t, the pressure sensing values sensed by the pressure sensors PS5-PS8 at the time point t and equation (1). The processing circuit 20 calculates a COG movement vector by subtracting the COG coordinate COG(t−1) of the time point t−1 from the COG coordinate COG(t) of the time point t. In addition, the inertial sensor IS1 disposed on the left shoe assembly 102 senses a movement direction on the horizontal x-y plane. Further, in Step S326, the processing circuit 20 compares the calculated COG movement vector with the movement direction sensed by the inertial sensor IS1. The processing circuit 20 determines whether an angle between a direction of the calculated COG movement vector and the movement direction sensed by the inertial sensor IS1 is greater than or equal to a third threshold angle value. The angle between the direction of the calculated COG movement vector and the movement direction sensed by the inertial sensor IS1 can be an inferior angle which is between 0 and 180 degrees. When the angle between the direction of the calculated COG movement vector and the movement direction sensed by the inertial sensor IS1 is greater than or equal to the third threshold angle value, this means that the COG variation of the right foot of the user is significantly different from the movement direction of the left foot of the user. Accordingly, the processing circuit 20 determines that the user is in an unsafe state and accordingly generates the determination result indicating that the user is in the unsafe state. Step S322 is then executed. When the angle between the direction of the calculated COG movement vector and the movement direction sensed by the inertial sensor IS1 is smaller than the second threshold angle value, the processing circuit 20 determines that the user is in a safe state accordingly. Step S328 is then executed.

In Step S328, the inertial sensor IS2 disposed on the right shoe assembly 104 is configured to sense a tilt angle with respect to the horizontal plane. The processing circuit 20 compares the tilt angle sensed by the inertial sensor IS2 with a first threshold angle value for determining whether the user is standing on a flat ground or a slope ground. The first threshold angle value can be an angle of repose or a critical angle of repose, but not limited thereto. In an embodiment, when the tilt angle sensed by the inertial sensor IS2 is greater than or equal to the first threshold angle value, this means the user may be standing on a slope ground. Step S322 is then executed and the alarm module 30 outputs an alarm signal to notify that the user is in an unsafe state. When the tilt angle sensed by the inertial sensor IS2 are smaller than the first threshold angle value, this means the user may be standing on a flat ground.

In Step S322, the alarm module 30 outputs an alarm signal for performing an alarm function according to the determination result of Step S318, S320, S326 or S328. When the determination result of Step S318, S320, S326 or S328 indicates that the user is in the unsafe state or the user will be in an unsafe state, the alarm module 30 outputs the alarm signal to notify that the user is in an unsafe state and a fall event will occur for performing an alarm function. As such, through notification of the alarm signal, the user can immediately understand and be aware that a fall event will occur and take action to prevent falls. Therefore, through notification of the alarm module 30, the user can easily and immediately obtain a fall prediction alarm to avoid a fall accident. In addition, when the determination result of Step S318, S320, S326 or S328 indicates that the user is in the unsafe state or the user will be in an unsafe state, the processing circuit 20 can also send notification signal to the external device, so that the external device generates alarm signals or performs related fall alarm functions.

In addition, in Step S304, when the pressure sensing values sensed by the pressure sensors PS1-PS4 disposed on the left shoe assembly 102 and the pressure sensing values sensed by the pressure sensors PS5-PS8 disposed on the right shoe assembly 104 are smaller than the threshold value, Step S310, S320 or S328 is directly performed for determining whether the user is standing on a flat ground or a slope ground and accordingly determining the risk of falls based on the sensed tilt angle.

Note that, the wearable device 1 shown in FIG. 1 represents an exemplary embodiment of the invention, and those skilled in the art can make alterations and modifications accordingly. For example, the processing circuit 20 can utilize wireless transmission technologies, such as Bluetooth, Wi-Fi, mobile communication technologies (3G, 4G LTE, 5G), infra-red ray or radio frequency identification (RFID) to communicate with each pressure sensor, each inertial sensor, the alarm module 30 or external devices (e.g., exoskeleton robots, mobile communication devices) for transmitting signals, but not limited thereto. For example, the processing circuit 20 can utilize transmission interface technologies, such as universal asynchronous receiver/transmitter (UART) interface, inter-integrated circuit bus ($I^2C$ bus) interface, universal serial bus (USB) interface or controller area network bus (CAN bus) interface, to communicate with each pressure sensor, each inertial sensor, the alarm module 30 or external devices for transmitting signals, but not limited thereto. Please note that the procedure 3 is not limited to be executed according to the exact sequence shown in FIG. 3, if a roughly identical result can be obtained. The procedure 3 shown in FIG. 3 can include other intermediate steps or several steps can be merged into a single step or part of steps can be omitted for suitable modifications without departing from the spirit of the present invention. For example, Steps S308, S318 and S326 may be omitted. For example, Steps S310, S320 and S328 may be omitted. Such variation should also be included in the scope of the present invention.

On the other hand, regarding the installed position of the pressure sensors, as shown in FIG. 2, the shoe assembly 10 corresponds to the shape of the foot sole. The shape of the left shoe assembly 102 corresponds to the shape of the left foot sole of the user. The shape of the right shoe assembly 104 corresponds to the shape of the right foot sole of the user. The pressure sensors can be disposed on the metatarsal areas of the shoe assembly 10. When the user wears the wearable device 1, the metatarsal of the foot may contact with the pressure sensors disposed on the metatarsal area of the shoe assembly 10 and apply force on the pressure sensors disposed on the metatarsal area of the shoe assembly 10. For example, the pressure sensors PS1 and PS2 are disposed on the metatarsal area of the left shoe assembly 102. The pressure sensors PS5 and PS6 are disposed on the metatarsal area. The pressure sensors can also be disposed on the heel area or sole area of the left shoe assembly 102 and the right shoe assembly 104, but not limited thereto. Regarding the installed position of the inertial sensors, the inertial sensors can be disposed on a center or a COG of the pressure sensors. For example, as shown in FIG. 2, the inertial sensor IS1 is disposed on the left shoe assembly 102 and is disposed at a center of the pressure sensors PS1-PS4. The inertial sensor IS2 is disposed on the right shoe assembly 104 and is disposed at a center of the pressure sensors PS5-PS8. In addition, the processing circuit 20 can also be disposed on the left shoe assembly 102 or the right shoe assembly 104.

Those skilled in the art should readily make combinations, modifications and/or alterations on the abovementioned description and examples. The abovementioned steps of the procedure including suggested steps can be realized by means that could be hardware, firmware known as a combination of a hardware device and computer instructions and data that reside as read-only software on the hardware device, an electronic system or the above mentioned wearable device 1. Any of the abovementioned procedures and examples above may be compiled into program codes or instructions that are stored in a storage device. The processing circuit 20 may read and execute the program codes or the instructions stored in the storage device for realizing the abovementioned functions.

In summary, the embodiments of the present invention can predict the trend of the center of gravity of the human body and measure the sole posture by using the sensing values of the pressure sensors and inertial sensors disposed on the shoe assembly, accordingly determine whether the user is at risk of falling and inform the user about the unsafe state through outputting the alarm signal, thus, effectively improving the safety of users in their daily lives.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. A wearable device, comprising:
   a shoe assembly;
   a plurality of pressure sensors, disposed on the shoe assembly and configured to generate a plurality of pressure sensing values;
   a processing circuit, configured to calculate a center of gravity coordinate according to the plurality of pressure sensing values and coordinates of the plurality of pressure sensors, wherein the processing circuit is configured to calculate a movement speed moving from a previous calculated center of gravity coordinate to a current calculated center of gravity coordinate, calculate a predicted center of gravity coordinate according to the calculated movement speed and a movement direction from the previous calculated center of gravity coordinate to the current calculated center of gravity coordinate, and determine whether the predicted center of gravity coordinate is located within a safety area to generate a determination result, wherein the safety area is within an area formed by pressure sensors disposed inside a first assembly of the shoe assembly and pressure sensors disposed inside a second assembly of the shoe assembly; and
   an alarm module, configured to output an alarm signal to perform an alarm function when the determination result indicates that the predicted center of gravity coordinate is not located within the safety area.

2. The wearable device of claim 1, further comprising:
   a plurality of inertial sensors, each configured to measure a tilt angle;
   wherein the processing circuit determines whether the tilt angle is greater than or equal to a threshold angle value to generate the determination result and the alarm module outputs the alarm signal to perform the alarm function when the determination result indicates that the tilt angle is greater than or equal to the threshold angle value.

3. The wearable device of claim 1, wherein the shoe assembly includes a first assembly and a second assembly, the plurality of pressure sensors include a plurality of first pressure sensors and a plurality of second pressure sensors, the plurality of first pressure sensors are disposed on the first assembly, and the plurality of second pressure sensors are disposed on the second assembly.

4. The wearable device of claim 3, wherein the plurality of first pressure sensors disposed on the first assembly are divided into a first group of pressure sensors and a second group of pressure sensors, a sensing value sensed by each of the first group of pressure sensors is greater than a sensing value sensed by each of the second group of pressure sensors, wherein the processing circuit calculates a center of gravity coordinate of the first group of pressure sensors and a center of gravity coordinate of the second group of pressure sensors, calculates a trend vector of center of gravity by subtracting the center of gravity coordinate of the second group of sensors from the center of gravity coordinate of the first group of sensors, the processing circuit determines whether an angle between a direction of the calculated trend vector of center of gravity and a movement direction sensed by an inertial sensor disposed on the second assembly is greater than or equal to a first threshold angle value to generate the determination result and the alarm module outputs the alarm signal to perform the alarm function when the determination result indicates that the angle between the direction of the calculated trend vector of center of gravity and the movement direction sensed by the inertial sensor disposed on the second assembly is greater than or equal to the first threshold angle value.

5. The wearable device of claim 3, wherein the processing circuit calculates a center of gravity coordinate of a first time point according to coordinates of the plurality of first pressure sensors at the first time point and pressure sensing values sensed by the plurality of first pressure sensors at the first time point, calculates a center of gravity coordinate of a second time point according to coordinates of the plurality of first pressure sensors at the second time point and pressure sensing values sensed by the plurality of first pressure sensors at the second time point and calculates a center of gravity movement vector by subtracting the center of gravity coordinate of the second time point from the center of gravity coordinate of the first time point, wherein the processing circuit determines whether an angle between a direction of the calculated center of gravity movement vector and a movement direction sensed by an inertial sensor disposed on the second assembly is greater than or equal to a second threshold angle value to generate the determination result and the alarm module outputs the alarm signal to perform the alarm function when the determination result indicates that the angle between the direction of the calculated center of gravity movement vector and the movement direction sensed by the inertial sensor disposed on the second assembly is greater than or equal to the second threshold angle value.

6. The wearable device of claim 1, wherein the center of gravity coordinate is calculated by the processing unit according to the following equations:

$$COG(x_{COG}, y_{COG}) = \begin{cases} x_{COG} = \dfrac{\sum_{i=1}^{n} x_i P_i}{\sum_{i=1}^{n} P_i} \\ y_{COG} = \dfrac{\sum_{i=1}^{n} y_i P_i}{\sum_{i=1}^{n} P_i} \end{cases}$$

where $COG(X_{COG}, Y_{COG})$ represents the center of gravity coordinate, $X_{COG}$ represents an x-axis coordinate value of the center of gravity coordinate, $Y_{COG}$ represents a y-axis coordinate value of the center of gravity coordinate, $x_i$ represents the x-axis coordinate value of i-th pressure sensor, $P_i$ represents the pressure sensing value of i-th pressure sensor, $y_i$ represents the y-axis coordinate value of i-th pressure sensor, and n represents the number of the pressure sensors.

7. A method of operating a wearable device, the wearable device comprising a shoe assembly and a plurality of pressure sensors disposed on the shoe assembly, the method comprising:
 utilizing the plurality of pressure sensors to generate a plurality of pressure sensing values;
 calculating a center of gravity coordinate according to the plurality of pressure sensing values and coordinates of the plurality of pressure sensors;
 calculating a movement speed moving from a previous calculated center of gravity coordinate to a current calculated center of gravity coordinate and calculating a predicted center of gravity coordinate according to the calculated movement speed and a movement direction from the previous calculated center of gravity coordinate to the current calculated center of gravity coordinate;
 determining whether the predicted center of gravity coordinate is located within a safety area to generate the determination result, wherein the safety area is within an area formed by pressure sensors disposed inside a first assembly of the shoe assembly and pressure sensors disposed inside a second assembly of the shoe assembly; and
 outputting an alarm signal to perform an alarm function when the determination result indicates that the predicted center of gravity coordinate is not located within the safety area according to the determination result.

8. The method of claim 7, wherein the wearable device includes a plurality of inertial sensors, each inertial sensor is configured to measure a tilt angle, and the method further comprises:
 determining whether the tilt angle is greater than or equal to a threshold angle value to generate the determination result; and
 outputting the alarm signal to perform the alarm function when the determination result indicates that the tilt angle sensed by at least one of the plurality of inertial sensors is greater than or equal to the threshold angle value.

9. The method of claim 7, wherein the shoe assembly includes a first assembly and a second assembly, the plurality of pressure sensors include a plurality of first pressure sensors and a plurality of second pressure sensors, the plurality of first pressure sensors are disposed on the first assembly, and the plurality of second pressure sensors are disposed on the second assembly.

10. The method of claim 9, wherein the step of calculating the center of gravity coordinate according to the plurality of pressure sensing values and coordinates of the plurality of pressure sensors and generating the determination result according to the center of gravity coordinate and outputting the alarm signal to perform the alarm function according to the determination result comprises:
 dividing the plurality of first pressure sensors disposed on the first assembly into a first group of pressure sensors and a second group of pressure sensors, wherein a sensing value sensed by each of the first group of pressure sensors is greater than a sensing value sensed by each of the second group of pressure sensors;

calculating a center of gravity coordinate of the first group of pressure sensors and a center of gravity coordinate of the second group of pressure sensors and calculating a trend vector of center of gravity by subtracting the center of gravity coordinate of the second group of sensors from the center of gravity coordinate of the first group of sensors;

determining whether an angle between a direction of the calculated trend vector of center of gravity and a movement direction sensed by an inertial sensor disposed on the second assembly is greater than or equal to a first threshold angle value to generate the determination result; and outputting the alarm signal to perform the alarm function when the determination result indicates that the angle between the direction of the calculated trend vector of center of gravity and the movement direction sensed by the inertial sensor disposed on the second assembly is greater than or equal to the first threshold angle value.

11. The method of claim 9, wherein the step of calculating the center of gravity coordinate according to the plurality of pressure sensing values and coordinates of the plurality of pressure sensors and generating the determination result according to the center of gravity coordinate and outputting the alarm signal to perform the alarm function according to the determination result comprises:

calculating a center of gravity coordinate of a first time point according to coordinates of the plurality of first pressure sensors at the first time point and pressure sensing values sensed by the plurality of first pressure sensors at the first time point, and calculating a center of gravity coordinate of a second time point according to coordinates of the plurality of first pressure sensors at the second time point and pressure sensing values sensed by the plurality of first pressure sensors at the second time point;

calculating a center of gravity movement vector by subtracting the center of gravity coordinate of the second time point from the center of gravity coordinate of the first time point;

determining whether an angle between a direction of the calculated center of gravity movement vector and a movement direction sensed by an inertial sensor disposed on the second assembly is greater than or equal to a second threshold angle value to generate the determination result; and outputting the alarm signal to perform the alarm function when the determination result indicates that the angle between the direction of the calculated center of gravity movement vector and the movement direction sensed by the inertial sensor disposed on the second assembly is greater than or equal to the second threshold angle value.

12. The method of claim 7, wherein the step of calculating the center of gravity coordinate according to the plurality of pressure sensing values and coordinates of the plurality of pressure sensors determines the center of gravity coordinate according to the following equation:

$$COG(x_{COG}, y_{COG}) = \begin{cases} x_{COG} = \dfrac{\sum_{i=1}^{n} x_i P_i}{\sum_{i=1}^{n} P_i} \\ y_{COG} = \dfrac{\sum_{i=1}^{n} y_i P_i}{\sum_{i=1}^{n} P_i} \end{cases}$$

where $COG(X_{COG}, Y_{COG})$ represents the center of gravity coordinate, $X_{COG}$ represents an x-axis coordinate value of the center of gravity coordinate, $Y_{COG}$ represents a y-axis coordinate value of the center of gravity coordinate, $x_1$ represents the x-axis coordinate value of i-th pressure sensor, $P_1$ represents the pressure sensing value of i-th pressure sensor, $y_i$, represents the y-axis coordinate value of i-th pressure sensor, and n represents the number of the pressure sensors.

\* \* \* \* \*